US006928031B1

(12) United States Patent
Kanevsky et al.

(10) Patent No.: US 6,928,031 B1
(45) Date of Patent: Aug. 9, 2005

(54) ALARM CLOCK SYSTEM, METHOD OF OPERATION AND PROGRAM PRODUCT THEREFOR

(75) Inventors: Dimitri Kanevsky, Ossining, NY (US); Wlodek Zadrozny, Tarrytown, NY (US)

(73) Assignee: International Business Machines Corp., Armonk, NY (US)

( * ) Notice: Subject to any disclaimer, the term of this patent is extended or adjusted under 35 U.S.C. 154(b) by 0 days.

(21) Appl. No.: 09/557,119

(22) Filed: Apr. 24, 2000

(51) Int. Cl.[7] ........................ G04C 14/16; G04B 23/02
(52) U.S. Cl. ......................... 368/12; 368/10; 368/244; 368/250; 600/544
(58) Field of Search ................... 368/9, 10, 12, 368/244, 250, 251; 600/483, 484, 534, 552, 600/544, 26, 513–514, 545, 300; 340/575, 340/576

(56) References Cited

U.S. PATENT DOCUMENTS

| 4,228,806 A | * | 10/1980 | Lidow ........................ 368/12 |
| 4,836,219 A | * | 6/1989 | Hobson et al. ............. 600/595 |
| 4,999,772 A | * | 3/1991 | Bowman et al. ............ 600/484 |
| 5,101,831 A | * | 4/1992 | Koyama et al. ............ 600/500 |
| 5,187,657 A | * | 2/1993 | Forbes ........................ 600/513 |
| 5,259,390 A | * | 11/1993 | MacLean .................... 600/552 |
| 5,520,176 A | * | 5/1996 | Cohen ........................ 600/300 |
| 5,566,067 A | * | 10/1996 | Hobson et al. .......... 364/419.2 |
| 5,577,135 A | | 11/1996 | Grajski et al. |
| 5,846,206 A | * | 12/1998 | Bader ........................ 600/534 |
| 5,902,250 A | * | 5/1999 | Verrier et al. .............. 600/529 |
| 5,928,133 A | * | 7/1999 | Halyak ....................... 600/544 |

(Continued)

FOREIGN PATENT DOCUMENTS

DE          019509478    * 9/1996    .................. 368/244

(Continued)

OTHER PUBLICATIONS

"A New Standard for Integrating Polygraphic Sleep Recordings into a Comprehensive Model of Human Sleep and Its Validation in Sleep Disorders," The SIESTA project, http://www.ai.univie.ac.at/siesta, pp. 1-2, no date.

(Continued)

*Primary Examiner*—Kamand Cuneo
*Assistant Examiner*—Jeanne-Marguerite Goodwin
(74) *Attorney, Agent, or Firm*—Law Office of Charles W. Peterson, Jr.; Louis J. Percello (57) ABSTRACT

A programmable alarm clock system, method of operation and program product therefor with sleep analysis to identify and wake a person during non-REM sleep patterns, resulting in less subsequent drowsiness and better day-to-day functioning. The programmable alarm clock system includes at least one brain activity sensor attachable to a head of a sleeper. Brain activity signals from the sensor(s) are sent to a receiver at a local computer. The user, before retiring inputs a wake up time and attaches the sensor(s). The local computer sends brain activity signals to a remotely connected sleep analyzing server which analyzes the brain activity and identifies REM sleep periods and non-REM sleep periods. The labeled brain activity periods are returned to the local computer which waits for the wake up time. Then, the local computer sets an alarm time by adjusting the wake up time to coincide with a non-REM sleep period, if necessary and if possible. At the alarm time, the local computer sends a trigger to a remotely triggered local alarm device such as a clock, which sounds an alarm to wake the user/sleeper.

39 Claims, 5 Drawing Sheets

U.S. PATENT DOCUMENTS

| | | | |
|---|---|---|---|
| 5,999,846 A * | 12/1999 | Pardey et al. | 600/544 |
| 6,047,203 A * | 4/2000 | Sackner et al. | 600/483 |
| 6,142,950 A * | 11/2000 | Allen et al. | 600/529 |
| 6,547,728 B1 * | 4/2003 | Cornuejols | 600/300 |
| 6,595,929 B2 * | 7/2003 | Stivoric et al. | 600/549 |
| 6,605,038 B1 * | 8/2003 | Teller et al. | 600/300 |

FOREIGN PATENT DOCUMENTS

| | | | | |
|---|---|---|---|---|
| EP | 1163877 A1 * | 12/2001 | | |
| JP | 359023284 * | 2/1984 | | 368/10 |
| JP | 363205592 * | 8/1988 | | 368/244 |
| JP | 403017591 * | 1/1991 | | 368/238 |
| JP | 403017594 * | 1/1991 | | 368/244 |
| JP | 404319692 * | 11/1992 | | 368/244 |
| WO | WO009714354 A2 * | 4/1997 | | |

OTHER PUBLICATIONS

"The *SIESTA* recording protocol," http://www.ai.univie.ac.at/siesta/protocol.html, p. 1, no date.

*Protocol: Recording of Standardized All-Night Sleep Records*, (version 2.0, Jul. 1998) (17 pp.).

* cited by examiner

ALARM CLOCK SYSTEM, METHOD OF OPERATION AND PROGRAM PRODUCT THEREFOR

BACKGROUND OF THE INVENTION

1. Field of the Invention

The present invention generally relates to wake up alarm devices and, more particularly, to alarm clocks having a programmable alarm for waking a sleeper more naturally.

2. Background Description

Presently, there are several types of alarm clocks available to wake a sleeping person. These include, for example, alarm clocks with a bell alarm, a beeper, or a tone generator each repetitively generating a jarring sound as an alarm. Clock radios are an attempt to eliminate the unnatural repetitive tone alarm, replacing it with broadcast music, for example, in order to wake the sleeper to a more calmly and soothingly. Even some of these clock radio alarms include functions wherein the alarm, whether a bell, beep, or radio, begins at a quiet, low volume that gradually increases until someone turns off the alarm. This ramped volume gently and gradually wakes the sleeper, to avoid the jarring effect of the clanging bell of the traditional alarm clock.

Alarms have been developed more recently that further reduce the traumatic effect of being woken by a traditional alarm. One such product is clock that simulates dawn to create a natural alarm clock marketed presently in the US as the "Sunrise Alarm Clock," produced by Outside In (Cambridge) Ltd. These natural alarm clocks look like a bedside light with a built-in alarm clock. Simulating dawn gives the sleeper's internal body clock an opportunity to synchronize with the alarm, thereby, waking the person gently and more naturally. The manufacturer asserts that unlike traditional alarms, which may leave a person feeling groggy for several hours, after being awoken, the natural alarm allows the sleeper's system to adjust normally to the artificial dawn so that the person wakes up without the groggy feeling.

Although these natural wake-up alarm systems exhibit some degree of efficacy, they still do not accommodate another very important sleep factor known as rapid eye movement (REM) sleep. Numerous studies have been done on sleep and sleep disorders. From these studies, sleep has been characterized as alternately having periods of REM sleep (typically lasting 5–60 minutes) interspersed with periods of non-REM sleep (typically lasting about 90 minutes).

Further, it has been shown that how quickly one awakens depends upon whether the person is woken during non-REM or REM sleep. A person having been woken during REM sleep finds it harder to wake up and function normally, experiencing more subsequent drowsiness than if woken during non-REM sleep. Unfortunately, these prior art systems wake the sleeper at a specific time independent of whether the person is in non-REM or REM sleep.

It has also been shown that dreams occur during the REM sleep. Typically, those dreams are forgotten. Often, people struggle to remember recent dreams and dream interpretation is part of popular culture, see e.g., www.dream-analysis.com and see, dir.yahoo.com/Social_Science/Psychology/Branches/Sleep_and_Dreams. Waking during REM sleep or immediately thereafter would assist in remembering dreams.

Thus, there is a need for an alarm clock capable of waking sleepers during non-REM sleep with less resulting drowsiness, the awakened sleeper feeling refreshed and alert or, conversely to select having a recollection of some of the previous nights dreams.

OBJECTS OF THE INVENTION

It is a purpose of the present invention to assist in selecting a wake up time consistent with the most optimum period in which to be awoken;

It is another purpose of the present invention to allow a sleeper to set a wake up alarm time such that an alarm occurs during a sleeper's non-REM sleep periods;

It is yet another purpose of the present invention to allow a sleeper to set a wake up alarm time such that an alarm occurs during a sleeper's REM sleep periods;

It is yet another purpose of the present invention to allow select sounding a wake up alarm only during selected sleep periods.

SUMMARY OF THE INVENTION

The present invention is a programmable alarm clock system, method of operation and program product therefor with sleep analysis to identify and wake a person during REM, non-REM sleep patterns or other identifiable sleep patterns, such as a slow brain wave pattern. Sleepers awoken during a non-REM phase of sleep suffer less subsequent drowsiness and may function better during normal day-to-day activities. Sleepers awoken during REM sleep or immediately thereafter may be allowed to remember some of the previous evening's dreams.

The programmable alarm clock system includes at least one brain activity sensor attachable to a head of a sleeper. Brain activity signals from the sensor(s) are sent to a receiver at a local computer. Before retiring, the user inputs a wake up time, that may be in the form of a wake up command (e.g., "first REM phase after 6:30 am") and, then attaches the sensor(s). The local computer sends brain activity signals to a remotely connected sleep analyzing server which analyzes the brain activity and identifies REM sleep periods and non-REM sleep periods. The labeled brain activity periods are returned to the local computer which waits for the wake up time. Then, the local computer sets an alarm time by adjusting the wake up time to coincide with the selected wake up time/command, e.g., a non-REM sleep period, if necessary and if possible. At the alarm time, the local computer sends a trigger to a remotely triggered local alarm device such as a clock, which sounds an alarm to wake the user/sleeper.

BRIEF DESCRIPTION OF THE FIGURES

The foregoing and other objects, aspects and advantages will be better understood from the following detailed preferred embodiment description with reference to the drawings, in which.

DETAILED DESCRIPTION OF THE INVENTION

Figure 1:
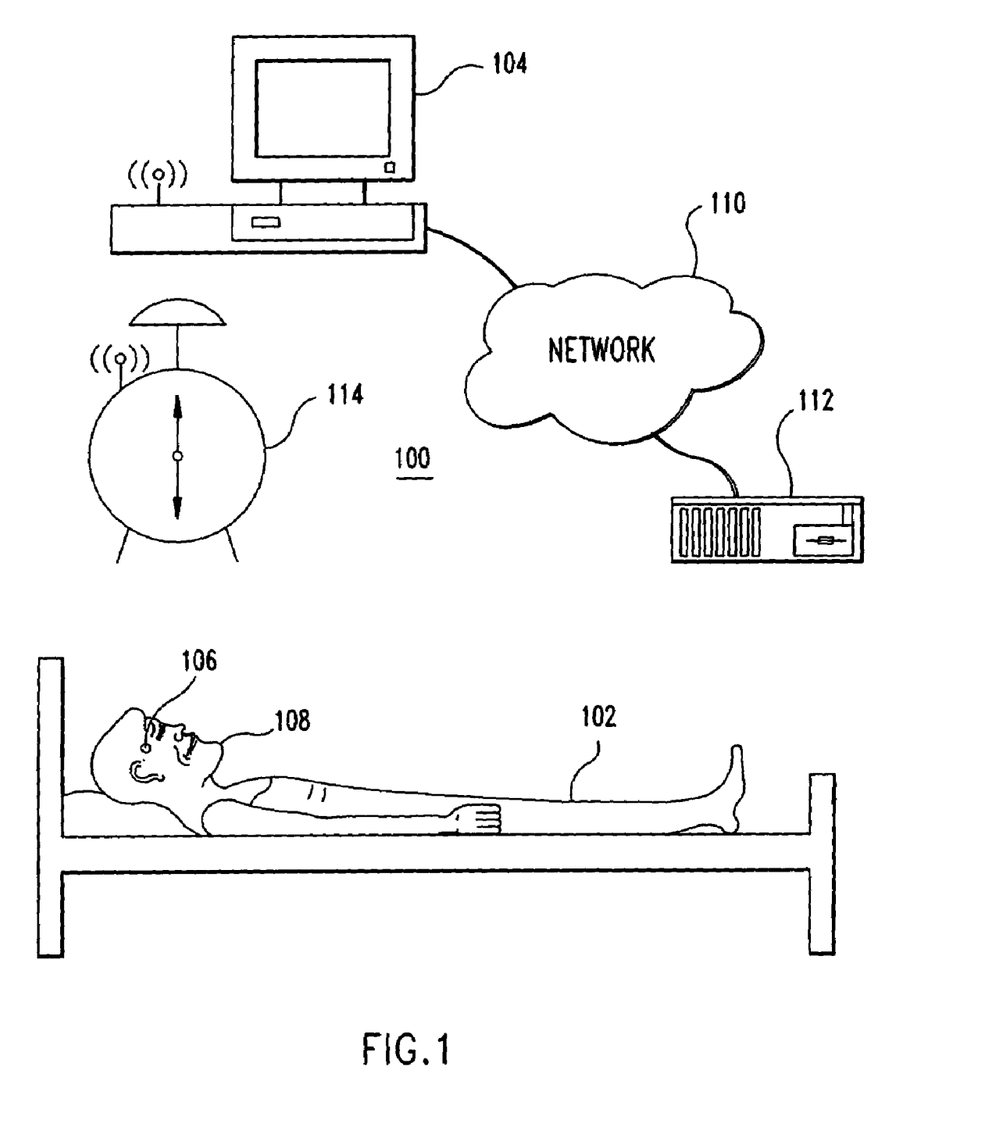
FIG. 1 is a block diagram of the preferred embodiment sleep analysis and alarm system 100 for waking a person during periods of non-REM sleep.

Referring now to the drawings, and more particularly, FIG. 1 is a block diagram of the preferred embodiment sleep analysis and alarm system arrangement 100 for waking a person 102 during selected periods of sleep. The arrangement includes a local computer 104, which may be a personal computer (PC) for local control. At least one wireless sensor 106 is attached to the eyelids or elsewhere on the head 108 of the sleeping person (sleeper) 102. The local computer is connected over a network 110 to a Computerized Sleep Analyzing Web Server (C-SAWS) 112. The network 110 may be a wireless network or, a more traditional wired network. The local computer 104 is in communication with a Local Alarm Device (LAD) 114 or clock. Optionally, the local computer 104 may be an embedded device, embedded in and part of the LAD 114. Further, the LAD 114 may include the C-SAWS 112 in addition to or independent of inclusion of the local computer 104.

Before retiring, the user 102 manually inputs a designated wake-up time (DWT) into the local computer 104 that acts as a controller. Alternately, the user 102 may select a preferred wake up pattern in lieu of selecting a DWT. Input may be made vocally through the microphone or manually. The DWT is taken as a target and passed to a Local Alarm Program (LAP) running in the local computer 104. After setting the alarm, the user 102 attaches non-intrusive wireless sensors 106 to strategic spots, e.g., the eyelids or elsewhere head 108. These sensors 106 attached to the head 108, which may be digital or analog, measure brain activity by measuring electrical signals using electroencephelography or polysomnography for example. The wireless eyelid sensors 106, which also may be digital or analog, detect eye movement and transmit appropriate signals to the local computer 104. Analog signals from analog sensors, when used, are converted to digital data in the local computer 104.

The local computer passes the digital brain activity information over a network 110 to C-SAWS 112. The network 110 may be a local area network (LAN) or, what is commonly referred to as the Internet or an Intranet. Local connection to the network may be a wired connection or wireless using infrared, radio, or by any suitable communication network allowing interconnection of computing devices for passing information. The C-SAWS 112 analyzes the brain activity information creating a brain activity or sleep chart. The C-SAWS 112 automatically detects slow wave sleep (SWS) patterns (normally referred to as deep sleep) or periods of REM, non-REM or other sleep activity using, for example, amplitude analysis, labeling the periods and recording the labeled information in a database. Multiple users can be connected to the C-SAWS 112 through individual computers 104, each running a LAP and communicating with the C-SAWS 112 over the Internet, for example. An alarm clock 114 may be connected directly to the local computer 104 or, remotely connected using appropriate wireless communication. Optionally, the wake up alarm may be sounded by the local computer 104 itself.

Figure 2:
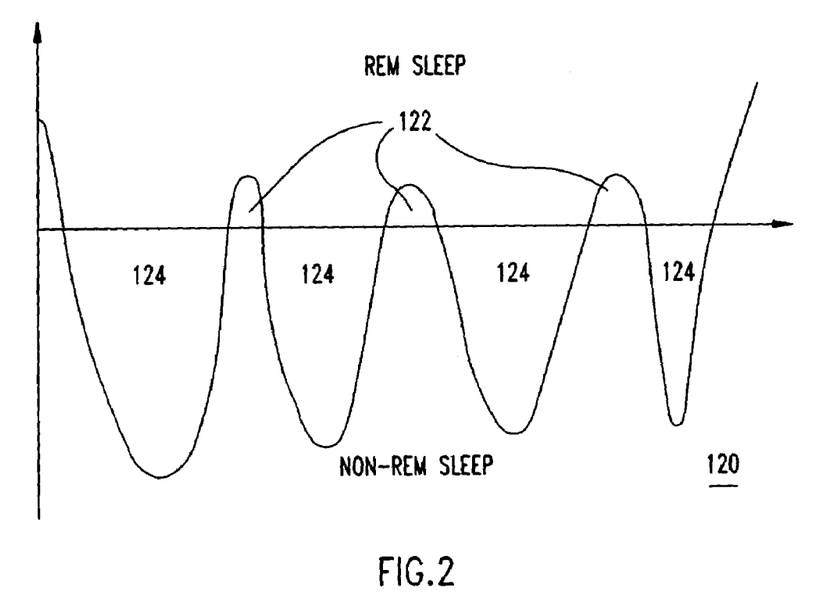
FIG. 2 is an example of a prototype sleep chart.

FIG. 2 is an example of creates a prototype sleep chart 120 for each particular user 102. Each sleep chart 120 may be displayed, locally, and used for statistical analysis of the particular user's sleep patterns. The sleep chart 120, which has areas labeled as REM periods 122 and non-REM periods 124, is sent back to the local computer 104. In the local computer 104, the LAP interrogates the chart 120 and decides when to initiate a wake up alarm. The chart 120 contains information identifiable by the LAP concerning when the sleeper 102 is experiencing REM sleep, non-REM sleep or other sleep patterns, and which the LAP can use to project future expected periods of REM sleep.

If the LAP determines that the DWT occurs during REM sleep, the LAP also decides an appropriate alternate time to wake the sleeper 102, whether before, after or during REM sleep. So, to provide guidance in selecting an appropriate time other than the DWT when the DWT falls within a REM sleep period 122, at the time that the user 102 designates the wake up time, the user 102 may also provide the LAP computer 104 with optional REM margins. The optional REM margins indicate how long before or after the DWT that the computer should advance or delay the alarm, if necessary, to avoid waking the sleeper 102 in REM sleep. If an early REM margin is not provided, then at the DWT the LAP computer 104 checks whether the sleeper 102 is in REM sleep and, if so, may postpone the alarm until it is anticipated that the sleeper 102 will enter a non-REM sleep period 124.

If an early REM margin is provided, then as the DWT approaches, using the sleeper's chart 120, the LAP projects whether the sleeper 102 will be in REM or non-REM sleep at the DWT. If it is determined that the sleeper 102 will be in REM sleep at the DWT, the alarm may be advanced or, tentatively, delayed according to previously selected user preferences or according to historical user preferences. If the alarm is tentatively delayed, the sleeper's sleep state is checked at the DWT for REM sleep and, the alarm is postponed if the sleeper 102 is in REM sleep. Otherwise, the alarm is issued at the DWT.

Thus, based on the above analysis, the LAP computer 104 issues the alarm, e.g., sending radio control signals to the wireless clock 114 or a clock radio which broadcasts the alarm to wake the sleeper 102. Alternatively, the sleeper 102 may be awakened using a traditional-like clock that is controlled by wired or wireless communication with the LAP computer or, a clock radio like wireless peripheral may be caused to play a previously selected specific message or song.

Figure 3:
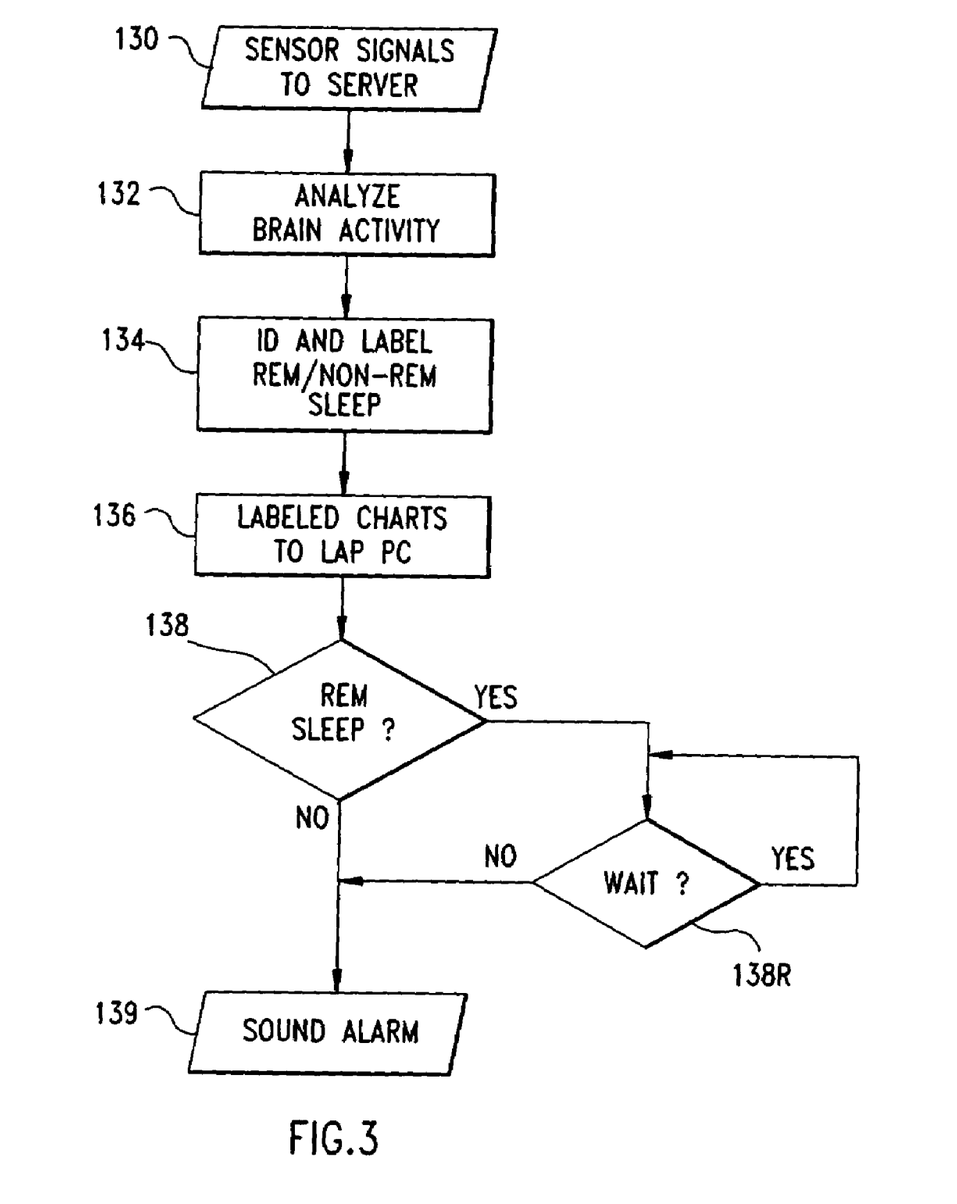
FIG. 3 is a flowchart of the steps of the preferred embodiment of the present invention.

FIG. 3 is an example of a flowchart of the preferred embodiment of the present invention for waking a sleeper 102 during a period of a selected sleep pattern. In the example of FIG. 3, non-REM sleep patterns are selected to wake the sleeper 102 feeling rested and alert. It is understood, however, that in addition to non-REM sleep patterns, other sleep patterns may be selected, for example, such as REM pattern periods, slow wave pattern periods, or any recognizable brain wave pattern periods. These types of sleep periods are provided for example only and not intended as a limitation. So, if a user 102 wishes to remember some of the previous nights dreams, the user 102 may select to be woken during REM sleep pattern period instead of non-REM sleep patterns.

Initially, in step 130 electronic signals from the sensors 106 on the sleeper's head are received and sent to a central server, the C-SAWS 112. The C-SAWS 112 analyzes the electronic signals in step 132 to create a brain activity chart. In step 134 the charted signals are labeled according to the type of selected sleep pattern, i.e., periods on the chart are identified and labeled as either REM sleep or non-REM sleep in this example. Then, in step 136, the labeled charts are sent to an appropriate local computer 104 for interrogation by the LAP. If the local computer 104 determines in step 138 that the sleeper 102 is currently experiencing non-REM sleep, then in 139 the local computer 104 initiates an alarm to wake the sleeper 102. Otherwise, if the sleeper 102 is in REM sleep, in 138R the local computer 104 must determine whether to wait until the end of a previously selected margin or to forcefully awaken the sleeper 102.

Figure 4:
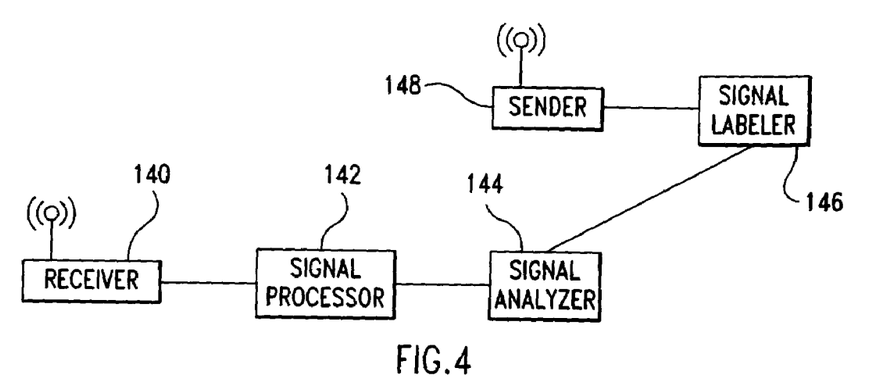
FIG. 4 is a block diagram of the preferred Computerized Sleep Analyzing Web Server in communication with one or more local PC through a network.

FIG. 4 shows a block diagram of the preferred Computerized Sleep Analyzing Web Server 112 in communication with one or more local (LAP) computer 104 through a network 110. The C-SAWS 112 receives brain activity information in Receiving Module 140 which passes the digitized signal to an optional Signal Processing Unit 142. The optional Signal Processing Unit 142 is included when some or all of the sensors 106 are analog. Analog signals from analog wireless sensors 106 are converted to digital signals by the Signal Processing Unit 142.

The digitized signal is then passed to the Signal Analyzer 144 which charts the data and automatically detects the selected sleep patterns based upon previous selected prototypes. The Signal Analyzer 144 passes the charted data to the Signal Labeler 146, which labels the chart with identified pattern areas labeled as REM periods or non-REM periods (in the example of FIG. 3) in a computer readable format acceptable by the local computer 104. When data is requested, a Sender 148 sends the labeled chart over the network, e.g., the Internet, to the requesting local computer 104.

Figure 5:
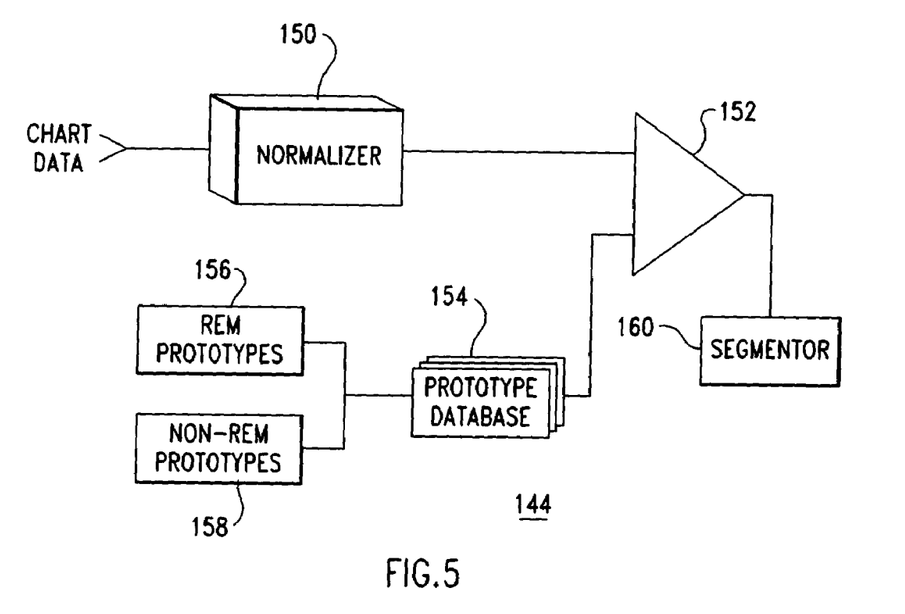
FIG. 5 is a block diagram of the Signal Analyzer which charts data passed to it from the Signal Processing Unit.

FIG. 5 is a block diagram of an example of the Signal Analyzer 144 which charts data passed to it from the Signal Processing Unit 142 or, when digital sensors 106 are employed, from the LAP unit (local computer 104). The chart data is input to a Normalizer 150 which converts the data to standard input format. The normalized data is sent to a Comparator 152 where it is compared with prototype data from a previous prototype database 154 that includes prototypical periods, REM periods 156 and non-REM periods 158 in the example of FIG. 3. These sleep pattern period prototypes may be generated using techniques such as taught in U.S. Pat. No. 5,577,135 entitled "Handwriting Signal Processing Front-End For Handwriting Recognizers" to Grajski et al., which is incorporated herein by reference. A Segmentator 160 separates the relevant pattern data, e.g., REM data from the non-REM data, and forwards the separated data to the Signal Labeler 146.

Prior to occurrence of the DWT and any selected early margin, the LAP computer 104 sends a message to C-SAWS 112 requesting a labeled chart for the sleeper 102 from the Signal Labeler 146. The labeled chart shows whether the user 102 is/will soon be experiencing a period of the selected sleep pattern, e.g., REM or non-REM sleep. Upon receiving the labeled chart, the LAP computer 104 initiates a decision maker process for deciding when to select as the best time to initiate an alarm. When the LAP computer 104 selects the best time to wake sleeper 102, the LAP may cause the local computer 104 to emit an alarm or, to transmit a signal to the LAD 114 to wake the sleeper 102. So, continuing the example of FIG. 3, if the sleeper 102 is in REM sleep, the local computer 104 waits until the designated REM margin passes before signalling the LAD 114 to wake sleeper 102.

Figure 6:
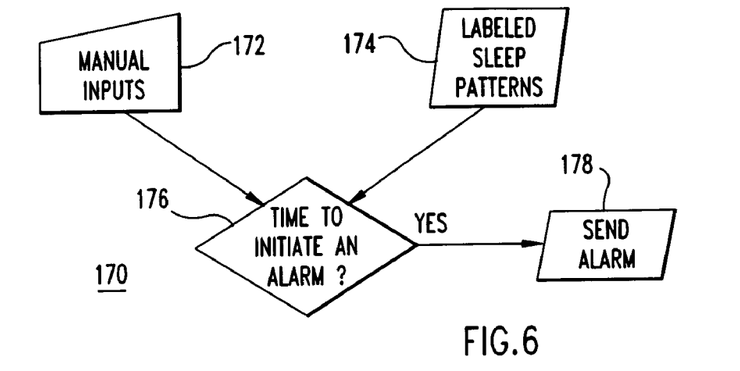
FIG. 6 is a block diagram of the preferred Local Alarm Program.

FIG. 6 is a block diagram of the preferred Local Alarm Program 170. The LAP 170 receives manual inputs 172 from a user 102 and labeled charts 174 from the C-SAWS 112. As noted above, the manual input 172 includes the DWT and wait (REM) margins. Also, the user 102 may indicate a priority, i.e., wherein the user 102 wishes to be woken even during REM or, whether the LAP 170 should wait up to an amount of time specified by the wait (REM) margin. Both types of inputs 172 and 174 are used in a Decision Maker 176 for deciding when to initiate an alarm in 178. The Decision Maker 176 chooses whether to send an alarm 178 immediately or, wait as long as the specified wait (REM) margin after the DWT as specified by user 102.

Figure 7:
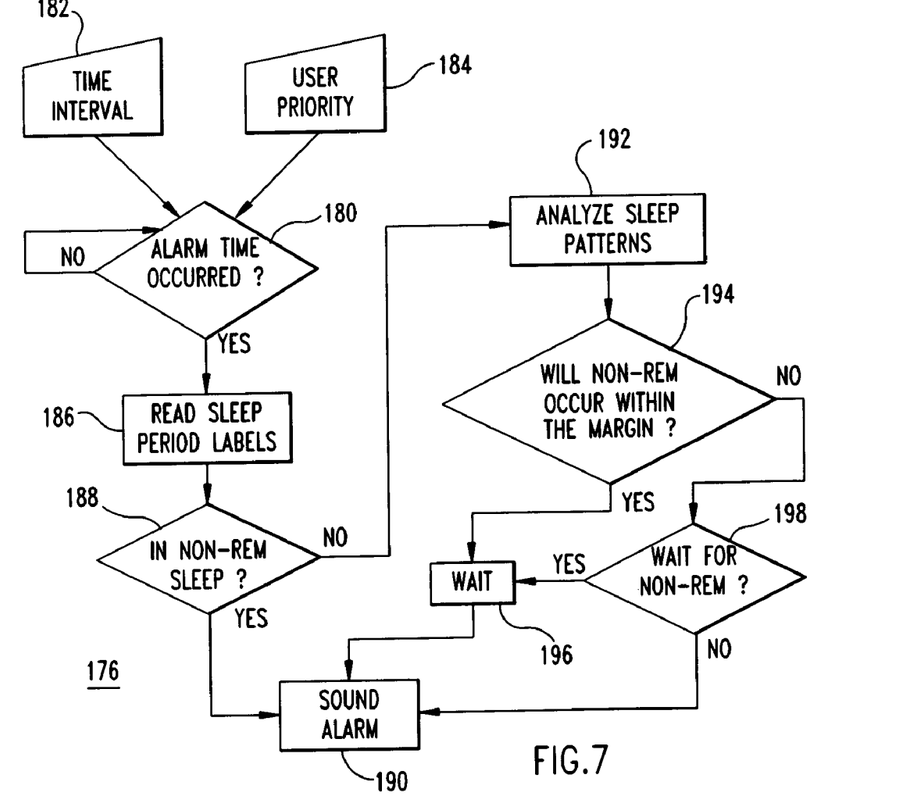
FIG. 7 is a flow chart of the preferred Decision Maker of the LAP of FIG. 6.

FIG. 7 is a flow chart of the preferred Decision Maker 176 of the LAP 170. In step 180, the decision maker periodically compares the given time interval input 182 and user priority input 184 to decide whether the alarm time has occurred. If not, then, the decision maker 176 waits, until the next time interval 182 occurs as determined by user priority input 184.

However, if the alarm time has occurred, the labeled chart received from the C-SAWS 112 is read in 186 to determine if the sleeper 102 currently is experiencing the selected sleep patterns in step 188, i.e., is in non-REM sleep in the example of FIG. 3. If the sleeper 102 is in non-REM sleep, then in step 190, the Decision Maker 176 sends a signal to initiate an alarm. If in this example, however, the sleeper 102 is in REM sleep, i.e., in step 186 determined not to be experiencing the selected sleep patterns, then, an appropriate alarm time must be determined. The sleeper's brain activity history or prior sleep patterns are analyzed in 192, checking previously collected data and sleep pattern prototypes. From the sleeper's brain activity history in 194 a determination is made whether the sleeper 102 will enter a selected sleep period (i.e., a non-REM sleep period) during the selected time interval 182. If in step 194, it is determined that selected sleep period will occur within the margin, then in step 196, the Decision Maker 176 waits for the selected sleep period.

Otherwise, if a period of the selected sleep will not occur, then in step 196 user priorities, provided as manual input 172, are checked to determine whether to wait or wake the user 102 during REM sleep. If the manual input 172 provides for waiting until the next selected sleep period occurence, then in 198 the Decision Maker 176 waits for selected sleep patterns to be identified by C-SAWS 112, which determine when the sleeper 102 is woken by an alarm signal initiated by the LAD.

As noted above, the description herein is in terms of non-REM sleep periods as being the selected wake up periods. It is understood however, that this is for example only and not intended as a limitation. It is also understood that in addition to non-REM sleep patterns, other sleep patterns may be selected such as REM pattern peroids, slow wave pattern periods, or any recognizable brain wave pattern periods.

While the invention has been described in terms of preferred embodiments, those skilled in the art will recognize that the invention can be practiced with modification within the spirit and scope of the appended claims.

We claim:

1. A programmable alarm clock system for waking a sleeper during a selected period of sleep, said programmable alarm clock system comprising:
   a sleep analyzing server;
   at least one sleep activity sensor attachable to a head of a sleeper;
   a receiver receiving sleep activity signals from at least one said sleep activity sensor;
   a local computer receiving a wake up time and received said sleep activity signals and sending said received sleep activity signals remotely to said sleep analyzing server; and a remotely triggered local alarm device sounding a wake up alarm responsive to a determination from said local computer that said sleeper should be awoken.

2. A programmable alarm clock system as in claim 1, wherein said sleep activity is brain activity and said sleep analyzing server analyzes received brain activity signals and identifies periods of slow wave sleep.

3. A programmable alarm clock system as in claim 1, wherein said sleep activity is brain activity and said sleep analyzing server analyzes received brain activity signals and identifies periods of REM sleep and non-REM sleep.

4. A programmable alarm clock system as in claim 1, wherein said at least one sensor measures brain activity using electroencephelography.

5. A programmable alarm clock system as in claim 1, wherein said at least one sensor measures brain activity using polysomnography.

6. A programmable alarm clock system as in claim 1, wherein said at least one sensor is a plurality of sensors measuring brain activity and in wireless communication with said local computer.

7. A programmable alarm clock system as in claim 6, wherein the server comprises:
a receiving module receiving sleep activity;
a signal analyzer charting sleep data and identifying sleep periods as being either selected activity sleep periods or other activity sleep periods;
a signal labeler labeling selected activity sleep periods and other activity sleep periods; and
a sender sending labeled said charts to the local computer.

8. A programmable alarm clock system as in claim 7, further comprising:
a signal processing unit receiving analog signals representative of said sleep activity and providing digital sleep data to the signal analyzer responsive to said analog signals.

9. A programmable alarm clock system as in claim 8, further comprising:
one or more sleep activity sensors attached to the head of said sleeper, each of said one or more sensors sending sleep activity signals to said receiving module.

10. A programmable alarm clock system as in claim 9, wherein at least one of said one or more sleep activity sensors is sensing brain activity.

11. A programmable alarm clock system as in claim 10, wherein the signal analyzer identifies sleep periods based upon selected brain activity prototypes.

12. A programmable alarm clock system as in claim 9, wherein at least one of said one or more sense activity sensors senses eye movement.

13. A programmable alarm clock system as in claim 1, wherein said at least one sleep activity sensor is one or more eyelid sensors are attached to said sleeper's eyelids measuring said eye movement, said receiver receiving sensor signals from said eyelid sensors.

14. A programmable alarm clock system as in claim 1, wherein said local computer is further provided with a selected sleep activity, the sleep analyzing server sending information about identified periods of said selected sleep activity to said local computer and said local computer determines from received said information when to trigger said wake up alarm relative to said wake up time.

15. A programmable alarm clock system as in claim 14, wherein when said local computer determines that said sleeper is in an identified period of said selected sleep activity at said wake up time, said local computer triggers said wake up alarm.

16. A programmable alarm clock system as in claim 15, wherein when said local computer determines that said sleeper is in an other sleep activity period identified as having a sleep activity other than said selected sleep activity at said wake up time, said local computer triggers said wake up alarm at an end to said other sleep activity period.

17. A programmable alarm clock system as in claim 16, wherein when said local computer determines that said sleeper is in an other sleep activity period identified as having a sleep activity other than said selected sleep activity at said wake up time, if said local computer determines that the next selected sleep activity period is expected to occur beyond a selected margin, said local computer triggers said wake up alarm.

18. A programmable alarm clock system as in claim 15, wherein when said local computer determines that said sleeper is in an other sleep activity period identified as having a sleep activity other than said selected sleep activity at said wake up time, said local computer postpones triggering said alarm until a next selected sleep period.

19. A programmable alarm clock system as in claim 14, wherein said selected sleep activity is REM sleep.

20. A programmable alarm clock system as in claim 14, wherein said selected sleep activity is non-REM sleep.

21. A method of operating a programmable alarm clock, said method comprising the steps of:
a) receiving brain activity signals and sending the brain activity signals to a remotely connected server,
b) digitizing said brain activity signals;
c) analyzing said digitized brain activity signals to identify selected sleep activity periods and other sleep activity periods;
d) waiting for a designated wake up time;
e) determining whether said brain activity signals indicate that a sleeper is in a period of said selected sleep activity or a period of other sleep activity at said designated wake up time; and
f) sounding an alarm at said designated wake up time if said brain activity signals indicate said selected sleep activity.

22. A method of operating a programmable alarm clock as in claim 21, when said brain-activity signals indicate said other sleep activity period at said wake up time, said method further comprising the steps of:
g) determining an alarm time to sound said alarm; and
h) sounding said alarm at said alarm time.

23. A method of operating a programmable alarm clock as in claim 22, wherein the determining step (g) comprises the steps of:
i) determining whether a wait margin has been selected, the alarm time being set to said designated wake up time when no wait margin has been selected;
ii) setting the alarm time when said next expected selected sleep activity period is within the wait margin; and
iii) if said other sleep activity continues beyond said wait margin, setting said alarm at the end of said wait margin.

24. A method of operating a programmable alarm clock as in claim 23, wherein the analyzing step (c) comprises the steps of:
i) creating a prototype chart of said digitized brain activity signals; and
ii) labeling periods in said prototype chart as being selected sleep activity periods and other sleep activity periods.

25. A method of operating a programmable alarm clock as in claim 24, wherein said prototype chart is sent to a local computer.

26. A method of operating a programmable alarm clock as in claim 25, wherein in the step (e) of determining whether sleep activity signals indicate that the sleeper is in the selected sleep activity period, said local computer interrogates the labeled prototype chart, determining therefrom whether the designated wake up time is in one of the selected sleep activity periods.

27. A method of operating a programmable alarm clock as in claim 26, wherein the local computer sends a trigger to an alarm clock in the steps (f) and (h) of sounding the alarm, the alarm clock sounding the alarm responsive to said trigger.

28. A method of operating a programmable alarm clock as in claim 27, wherein the selected sleep activity is non-REM sleep.

29. A method of operating a programmable alarm clock as in claim 27, wherein the selected sleep activity is REM sleep.

30. A method of operating a programmable alarm clock as in claim 27, wherein the selected sleep activity is slow wave sleep.

31. A computer program product for operating a programmable alarm clock system monitoring sleep activity and selecting a time to wake a monitored sleeper, said computer program product comprising a computer usable medium having computer readable program code thereon, said computer readable program code comprising:
   computer readable program code means for digitizing sleep activity signals;
   computer readable program code means for analyzing digitized said sleep activity signals to identify selected sleep periods and non-selected sleep periods;
   computer readable program code means for determining whether to send a trigger responsive to a designated wake up time is in a selected sleep period or non-selected sleep period; and
   computer readable program code means for sounding an alarm responsive to said trigger.

32. A computer program product for operating a programmable alarm clock system monitoring sleep activity and selecting a time to wake a monitored sleeper as in claim 31, wherein said computer readable program code means for determining an alarm time comprises:
   computer readable program code means for determining whether a wait margin has been selected, a trigger time being set to said designated wake up time when no wait margin has been selected;
   computer readable program code means for setting said trigger time as a next expected selected sleep activity period when said next expected selected sleep activity period is determined to be expected to occur within the wait margin; and
   computer readable program code means for setting said trigger time at the end of said wait main, when a non-selected sleep activity period is expected to extend through said wait margin.

33. A computer program product for operating a programmable alarm clock system monitoring sleep activity and selecting a time to wake a monitored sleeper as in claim 32, further comprising:
   computer readable program code means for forwarding received sleep activity signals to a remotely connected server.

34. A computer program product for operating a programmable alarm clock system monitoring sleep activity and selecting a time to wake a monitored sleeper as in claim 33, wherein the sleep activity signals are brain activity signals and said computer readable program code means for analyzing digitized brain activity comprises:
   computer readable program code means for creating a prototype chart of said digitized brain activity signals;
   computer readable program code means for labeling periods in said prototype chart as being selected sleep periods and non-selected periods; and
   computer readable program code means for sending each labeled said prototype chart to a local computer.

35. A computer program product for operating a programmable alarm clock system monitoring sleep activity and selecting a time to wake a monitored sleeper as in claim 34, wherein said computer readable program code means for sounding said alarm comprises:
   computer readable program code means for causing said local computer to send said trigger to a local alarm device.

36. A computer program product for operating a programmable alarm clock system as in claim 33, wherein said sleep activity signals are indicated by eye movement.

37. A computer program product for operating a programmable alarm clock system as in claim 36, wherein said selected sleep activity is REM sleep.

38. A computer program product for operating a programmable alarm clock system as in claim 36, wherein said selected sleep activity is non-REM sleep.

39. A computer program product for operating a programmable alarm clock system as in claim 36, wherein said selected sleep activity is slow wave sleep.

* * * * *